United States Patent [19]
Hirsch et al.

[11] Patent Number: 5,011,829
[45] Date of Patent: Apr. 30, 1991

[54] PHARMACEUTICAL COMPOSITION AND METHOD OF INHIBITING VIRUS

[75] Inventors: Martin S. Hirsch, Newton; Victoria A. Johnson, Boston, both of Mass.

[73] Assignee: G. D. Searle & Co., Skokie, Ill.

[21] Appl. No.: 360,439

[22] Filed: Jun. 2, 1989

[51] Int. Cl.$^5$ .................. A61K 31/70; A61K 31/445
[52] U.S. Cl. ...................................... 514/50; 514/315; 514/934
[58] Field of Search ..................... 514/315, 50, 934

[56] References Cited

U.S. PATENT DOCUMENTS

| | | | |
|---|---|---|---|
| 4,724,232 | 2/1988 | Rideout et al. | 514/50 |
| 4,849,430 | 7/1989 | Fleet et al. | 514/315 |
| 4,857,511 | 8/1989 | Rideout et al. | 514/50 |

FOREIGN PATENT DOCUMENTS 282618 9/1988 European Pat. Off.
63-175354 2/1989 Japan.

OTHER PUBLICATIONS

Pollner, Medical World News, Dec. 11, 1989, p. 53.
Johnson et al., Antimicrobial, Agents & Chemother, 33, 53–57 (1989).
Hartshorn et al., Antimicrobiol. Agents & Chemother. 31, 168–172 (1987).
Hirsch & Kaplan, Antimicrobiol. Agents & Chemother. 31, 839–843 (1987).
Johnson et al., IV Inter. Conf. Aids, Jun. 12–16, 1988, Stockholm, Sweden.
Johnson et al., J. Infect. Diseases 159, 837–844 (1989).
Spector et al., Infect. Diseases 159, 822–828 (1989).
Fleet et al., Febs Lett. 237, 128–132 (1988).
Karpas et al., Proc. Natl. Acad. Sci. U.S.A. 85, 9229–9233 (1988).
Walker et al., Proc. Natl. Acad. Sci. U.S.A. 84, 8120–8124 (1987).
Poli et al., Science 244, 575–577 (1989).
Anon., Science 244, 511 (1989).
Hirsch and Kaplan, Scie. Amer. 256, 76–85 (1987).

*Primary Examiner*—Jerome D. Goldberg
*Attorney, Agent, or Firm*—Scott J. Meyer; Paul D. Matukaitis; James W. Williams, Jr.

[57] ABSTRACT

A pharmaceutical composition and a method of inhibiting human immunodeficiency virus (HIV) is disclosed which comprises administering to an HIV infected patient a synergistic combination of 3'-azido-3'-deoxythymidine (AZT) and N-butyl deoxynojirimycin (N-butyl DNJ) in an amount which achieves antiviral efficacy.

21 Claims, No Drawings

PHARMACEUTICAL COMPOSITION AND METHOD OF INHIBITING VIRUS

BACKGROUND OF THE INVENTION

This invention relates to a pharmaceutical composition and method of inhibiting human immunodeficiency virus (HIV) and, more particularly, to a synergistic combination of the N-butyl derivative of 1,5-dideoxy-1,5-imino-D-glucitol (deoxynojirimycin) and 3'-azido-3'-deoxythymidine (AZT) in amount which achieves antiviral efficacy, having potential use for the treatment of acquired immune deficiency syndrome (AIDS) and AIDS related complex (ARC).

Acquired immune deficiency syndrome, which only a few years ago was a medical curiosity, is now a serious disease. As a consequence, a great effort is being made to develop drugs and vaccines to combat AIDS. The AIDS virus, first identified in 1983, has been described by several names and has the capacity to replicate within cells of the immune system and thereby lead to a profound destruction of T4. T-cells (or CD4+cells). See, e.g., Gallo et al., Science 224, 500–03 (1984), and Popovic et al., Ibid., 497–500 (1984).

This virus, which has been established to be a retrovirus, had been known as lymphadenopathy-associated virus (LAV) or AIDS-related virus (ARV). Two distinct AIDS viruses, HIV-1 and HIV-2, have been described. HIV-1 is the virus originally identified in 1983 by Montagnier and co-workers at the Pasteur Institute in Paris [Ann. Virol. Inst. Pasteur 135 E, 119–134 (1984)], while HIV-2 was more recently isolated by Montagnier and his coworkers in 1986 [Nature 326, 662 (1987)]. As used herein, HIV is meant to refer to these viruses in a generic sense.

Although the molecular biology of AIDS is beginning to be unraveled and defined, much more needs to be learned and understood about this disease. In the meantime, numerous approaches are being investigated in the search for potential anti-AIDS drugs and vaccines. Development of an AIDS vaccine is hampered by lack of understanding of mechanisms of protective immunity against HIV, the magnitude of genetic variation of the virus, and the lack of effective animal models for HIV infection. See, for example, Koff and Hoth, Science 241, 426–432 (1988).

One approach to designing drugs or vaccines for treating human beings infected by HIV depends on the knowledge molecular biologists have acquired on the replicative life cycle of the virus as it enters and infects a host cell, replicates, and goes on to infect other cells. Within the replicative cycle of HIV there are certain virus-specific steps which are potential targets for antiviral therapy. Hirsch et al., Antimicrob. Agents Chemother. 31, 839–43 (1987).

The first drug to be approved by the U.S. Food and Drug Administration (FDA) for treatment of AIDS was zidovudine, better known under its former name azidothymidine (AZT). Chemically, this drug is 3'-azido-3'-deoxythymidine, and has the following structure:

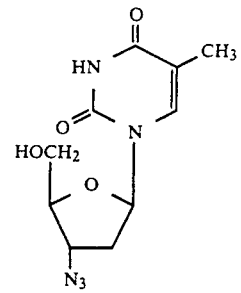

AZT is converted by cellular kinases to a triphosphate form which is a strong competitive inhibitor of HIV reverse transcriptase, thus interfering with an early stage in HIV replication.

This drug was originally selected as a potential weapon against AIDS because it was shown to inhibit replication of the virus in vitro. Such tests are virtually the only practical method of initially screening and testing potential anti-AIDS drugs.

Although AZT is now used clinically, a serious drawback of AZT is its toxic side-effects. Indeed, the FDA required package insert for Retrovir ®, the commercially available pharmaceutical composition containing AZT as the active ingredient, warns of hematologic toxicity including granulocytopenia and severe anemia requiring transfusions. Thus, the search for better anti-AIDS drugs continues.

More recently, certain glucosidase inhibitors have been tested for activity against the AIDS virus. Because the envelope glycoproteins of HIV are heavily glycosylated, compounds that interfere with co- and posttranslational processing of glycoprotein gp120 and the transmembrane glycoprotein gp41 may prevent viral entry into a cell. Karpas et al., Proc. Natl. Acad. Sci. USA 85, 9229–9233 (1988). These compounds interfere, or interrupt a different stage in the HIV replicative process than AZT.

Three such compounds suggested as potential anti-AIDS drugs are castanospermine, 1-deoxynojirimycin (DNJ) and 2,5-dihydroxymethyl-3,4-dihydroxy-pyrrolidine (DMDP). See, e.g., Sunkara et al., Biochem. Bioohvs. Res. Commun. 148(1), 206–210 (1987); Tyms et al., Lancet, Oct. 31, 1987, pp. 1025–1026; Walker et al., Proc. Natl. Acad. Sci. USA 84, 8120–8124 (1987); and Gruters et al., Nature 330, 74–77 (1987).

Thus, castanospermine, which is an alkaloid isolated from the seeds of Australian chestnut tree, has been found to interfere with normal glycosylation of HIV virions, thereby altering the envelope glycoprotein and preventing entry of HIV into target cells. However, since castanospermine is in limited supply due to its natural source, it is extremely expensive, and therefore not a realistic candidate for a drug urgently required on a large scale. Additionally, castanospermine has demonstrated cytotoxicity at dose levels of 0.70 mg/ml. Karpas et al., Proc. Nat'l. Acad. Sci. USA 85, 9229–9233 (1988).

In PCT Inter. Appln. WO 87/03903, published July 2, 1987, the N-methyl derivative of deoxynojirimycin (DNJ) also was disclosed as having activity against HIV ostensibly based on its glucosidase I inhibitory activity. However, it was subsequently shown by Fleet et al., FEBS Lett 237, 128–132 (1988), that not all glucosidase I inhibitors are effective inhibitors of HIV.

Therefore, some other mechanism may be responsible for HIV inhibitory activity.

The N-butyl derivative of deoxynojirimycin (N-butyl DNJ) has been found to have enhanced inhibitory activity against the human immunodeficiency virus (HIV) at non-toxic concentrations compared to that exhibited by the corresponding N-methyl and N-ethyl derivatives.

N-butyl DNJ has the following chemical structure:

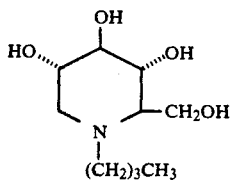

In order to indicate stereoisomerism, solid and dotted lines show bonds directed above or below, respectively, the plane of the paper.

N-butyl DNJ uniquely reduces the virus titer by over five logs at non-cytotoxic concentrations whereas the N-methyl- and N-ethyl-deoxynojirimycin derivatives cause only a two to four log-order of reduction in the yield of infectious HIV. As such, the N-butyl derivative has significant potential use for the treatment of acquired immune deficiency syndrome (AIDS), and phase I clinical trials of this agent have recently been announced.

Despite the above noted advances made in drug therapy for HIV infected individuals, it is believed that effective non-toxic therapy directed against HIV may require a chemotherapeutic approach which involves the use of combination therapies. Such an approach has not been widely employed in anti-HIV therapy, but has been successful in the treatment of a variety of bacterial and fungal infections, as well as in cancer chemotherapy. Combinations of anti-HIV therapies which include agents that attack the HIV replicative cycle at multiple sites offer several advantages, particularly if favorable drug interactions occur.

When two agents are combined, they may have one of three types of activity against HIV replication in vitro, as established by the Combination Index (CI) discussed hereinafter.

1. Additive effect: Two drugs are said to be additive when the activity of the drugs in combination is equal to the sum (or a partial sum) of their independent activities when studied separately.

2. Synergism: The combined effect of a synergistic pair of agents is greater than the sum of their independent activities when measured separately.

3. Antagonism: If two drugs are antagonistic, the activity of the combination is less than the sum of their independent effects when measured alone.

The goals of combination therapy should include the ability to target different sites in the HIV replicative cycle, and to affect viral replication in a broad range of cell types. Also, the agents should not display additive toxicity in combination. The benefits of combination therapy include potentially additive or synergistic interactions in vitro, which may allow the use of individual drugs below their toxic concentrations. Also, combination therapy may prevent the emergence of drug-resistant HIV mutants.

Studies combining various known anti-HIV agents have already been conducted. For example, combinations of either AZT or 2',3'-dideoxycytidine and recombinant alpha-A interferon have been shown to inhibit HIV synergistically in vitro. Hartshorn et al., *Antimicrob. Ag. Chemother.* 31, 168-72 (1987); Vogt et al., *J. Infect. Dis.* 158, 378-85 (1988). Other combinations, such as AZT plus acyclovir have shown synergism. Mitsuya et al. in S. Broder (ed.) AIDS, Modern Concepts and Therapeutic Challenges, Marcel Dekker, Inc., N.Y. However, other tested drug combinations such as AZT and ribavirin (1,$\beta$-D-ribofuranosyl-11-1,2-triazole-3-carboxamide) have been shown to be antagonistic in vitro. Vogt et al., *Science* 23, 1376-79 (1987).

BRIEF DESCRIPTION OF THE INVENTION

In accordance with the present invention, we have now discovered that the combination of N-butyl DNJ and AZT inhibits HIV synergistically without additive toxicity in vitro. Thus, lower doses of each AZT and N-butyl DNJ may be used, thus minimizing the toxic side effects of each, particularly those associated with AZT.

Suitable dosages to treat humans suffering from AIDS or ARC for the AZT component of the combination of the present invention range from about 50 mg/day to about 1.2g/day.

Suitable dosages to treat humans suffering from AIDS or ARC for the N-butyl DNJ component of the combination of the present invention range from about 1 mg/kg/day to about 500 mg/kg/day. Toxicity studies in experimental animals have established that N-butyl DNJ has a low toxicity.

The drugs should be combined in amounts sufficient to achieve the additive or synergistic benefits of their combination.

DETAILED DESCRIPTION OF THE INVENTION

While the specification concludes with claims particularly pointing out and distinctly claiming the subject matter regarded as forming the invention, it is believed that the invention will be better understood from the following description.

Source of AZT and N-butyl DNJ

The AZT was obtained in powder form from Dr. P. A. Furman, Burroughs-Wellcome Co., Research Triangle Park, N.C. It was dissolved in sterile phosphate-buffered saline and stored at a concentration of 1 mM in aliquots of 0.5 ml/vial at $-20°$ C. prior to use.

The N-butyl DNJ was obtained in powder form from Dr. R. Mueller, G. D. Searle & Co. It was stored in powder form at $4°$ C. until used, and fresh drug solutions were prepared for each medium change. The N-butyl DNJ was dissolved in sterile-filtered double-distilled water, and then sterile filtered prior to the preparation of drug dilutions.

Assays Of Anti-Viral Activity

In these examples, we evaluated the antiviral activities of various combinations of this invention using modifications of various in vitro assays used to study anti-viral agents [Ho et al., *Lancet*, 1, pp. 602-04 (1985); Hartshorn et al., *Antimicrob. Ag. Chemother.* 30. 189-91 (1986)].

For each of these assays, we cultured uninfected H9 cells, a gift from Dr. Robert C. Gallo, National Cancer Institute, Bethesda, Maryland, [Popovic et al., *Science.* 224, pp. 497-500 (1984)] at an initial concentration of $0.4 \times 10^6$ cells/ml in 5 ml final volume of R-20 culture medium comprising RPMI-1640 medium, 20% heat-inactivated fetal calf serum (Sigma Chemical, St. Louis, Mo.), L-glutamine (2mM), and antibiotics (penicillin, 250 U/ml and streptomycin, 250 μg/ml) in a T-25 flask (Falcon, Becton Dickinson Laboratory, Lincoln Park, N.J.).

In the experiments, uninfected H9 cells ($2 \times 10^6$ cells) were suspended in 5 ml of R-20 medium in T-25 flasks. The multiplicity of infection was 250 tissue culture (obtained from Dr. Robert C. Gallo) per $1 \times 10^6$ cells. infectious doses ($TCID_{50}$) of cell-free HIV-1 (HTLV-IIIB) See Hartshorn et al., *Antimicrob. Ag. Chemother.* 31, 168-72 (1987). The culture medium was changed on days 4, 7 and 11, with 2 ml of cell suspension being resuspended in 5 ml of replacement medium COntaining the original concentrations of antiretroviral agent(s). Various graded concentrations of N-butyl DNJ or AZT, either alone or in combination, were added to the cell cultures simultaneously with the HIV-1 isolate. The culture medium was exchanged on days 4, 7 and 11 and again N-butyl DNJ, AZT, or both, were added with the medium changes to maintain the concentration of each of those agents originally present. In these assays, cell-free supernatants of the cultures were harvested on one or more of days 7, 11, and 14 for determination of HIV-1 core antigen p24 production, viral reverse transcriptase activity (RT) or yield of infectious virus to evaluate the effects of the agents alone, or in combination, on HIV replication in vitro. For each virus replication assay, uninfected cells were exposed to HIV-1 inoculum without a subsequent wash. Simultaneously, multiply-diluted fixed-ratio combinations of agents, or single agents, were added to each flask. We assessed cell proliferation and viability by the trypan blue dye exclusion method. In all assays, uninfected and infected cultures were maintained in parallel. Drug-treated toxicity controls were maintained at the highest concentration of each agent tested (either alone or in combination), to exclude an anti-HIV-1 effect due to an antiproliferative effect of either agent tested.

Reverse Transcriptase Assay

We measured reverse transcriptase activity as an indicator of the effects of combinations of AZT and N-butyl DNJ according to this invention on HIV viral replication [as described by Popovic et al., *Science*, 224, 497-500 (1984); Gallo et al., *Science*, 224, 500-03 (1984); or Ho et al., *Proc. Natl. Acad. Sci. USA*, 81, 7588-90 (1984); Ho et al., *Science*. 226, 451-53 (1984)]

More specifically, in the reverse transcriptase assay, we employed the reagents listed below. The dithiothreitol (DTT) was obtained from Boehringer Mannheim Bio-Chemicals, Indianapolis, Ind. The PEG 8000 (polyethylene glycol) was obtained from Fisher Scientific, Medford, Mass. The tRNA used was type X-S, obtained from Sigma Chemical, St. Louis, Mo. The 3H-TTP (tritiated thymidine triphosphate) was obtained from DuPont, New England Nuclear Research Products, Boston, Mass.

| Buffer A | |
|---|---|
| *1.0 M Tris (pH 7.8) | 1.25 ml |
| *0.1 M Ethylenediamine tetraacetic acid | 12.5 ml |
| *10% Triton X-100 | 1.25 ml |
| *Glycerol | 250.00 ml |
| Water | 235.10 ml |
| DTT (crystal) | 0.77 g |
| KCl (crystal) | 3.72 g |
| | 500.00 ml |
| Solution 2 | |
| *10% Triton X-100 | 45.00 ml |
| double distilled water | 45.00 ml |
| KCl (crystal) | 1.63 g |
| | 500.00 ml |
| PEG (30%), 0.4 M NaCl | |
| PEG 8000 | 150.00 g |
| NaCl | 11.70 g |
| Water | to 500.00 ml |
| Trichloroacetic Acid (TCA) (10%) | |
| TCA | 50.00 g |
| Sodium pyrophosphate | 4.46 g |
| Water | to 500.00 ml |
| Trichloroacetic Acid (5%) | |
| TCA | 1000.00 g |
| Sodium pyrophosphate | 178.00 g |
| Water | to 20.00 l |

*Solutions made in distilled water.

Universal Buffer 0.01 M Tris (pH 8.0) and 0.015 M NaCl solution 0.2 M Dithiothreitol 0.309 g DTT
10.0 ml universal buffer This solution was stored frozen at −20° C. and thawed only once before use.

10 mg/ml tRNA tRNA was made 10 mg/ml in universal buffer and stored at 20° C.

10 units/ml dA or rA template

Oligo dT template primers (#27-7878 and #27-7868, Pharmacia/P-L Biochemicals, Piscataway, N.J.) were dissolved in 2.5 ml universal buffer to give a 10 unit/ml solution. The solution was stored in 0.5 ml aliquots at −20° C. and thawed before use.

We carried out PEG precipitation of virus particles from cell-free supernatants by adding to 2 or 3 ml of clarified culture supernatant fluid, one-half as much of the PEG precipitation solution, vortexed well and placed the mixture on ice overnight at 4° C. We then centrifuged at 800 times gravity (−2100 rpm) minutes to pellet precipitate. Subsequently, we aspirated off all the supernatant fluid, let the precipitate stand, then aspirated again to provide a dry pellet. We then resuspended the precipitate in a buffer comprising 100 μl buffer A and 50 μl solution 2, where the original supernatant used was 2 ml, with proportionate volumes of resuspension buffer being used for different volumes of supernatant fluid. We resuspended the pellet by placing a pasteur pipette in the tube and vortexing. We froze the sample at −20° C. if not assayed immediately. All the steps of the PEG precipitation were carried out using capped centrifuge tubes. Any step requiring exposure to air was carried out in a biohazard hood until after the addition of buffer A and solution 2, which inactivated the virus.

We assayed samples using the following reverse transcriptase (RT) cocktail:

| RT cocktail | rA cocktail X # samples (μl/tube) | dA cocktail X # samples (μl/tube) |
| --- | --- | --- |
| 1 M Tris (pH 7.8) | 4 | 4 |
| 0.2 M DTT | 4 | 4 |
| 0.2 M MgCl$_2$ | 5 | 5 |
| double-distilled water | 47 | 47 |
| Universal buffer | 22.5 | 22.5 |
| 3H-TTP | 2.5 | 2.5 |
| Oligo dT, poly rA (or dA) | 5 | 5 |

We prepared the RT cocktail by multiplying the volume of reagents by the number of samples plus 2 for controls (the dA cocktail was an internal negative control) plus 2 for pipetting loss. Subsequently, we added 90 μl of rA or dA cocktail to eppendorf tubes kept in an ice-water bath (1 rA and 1 dA tube for each sample). We then added 10 μl of each sample to an rA and a dA tube, vortexed and then incubated in a 37° C. water bath for 1 hour.

In order to terminate reverse transcriptase activity, we removed samples from the water bath and placed them in an ice water bath. We then added 10 μl of cold tRNA solution to each tube, followed by 1 ml of cold 10% TCA solution. We let the tubes stand in the ice water bath for 20-30 minutes.

We then soaked 2.4 cm glass fiber filters (Millipore Corporation, Bedford, Massachusetts) in 5% TCA solution. We placed the filters on a sampling manifold (Millipore, Model 1225) attached to a vacuum source. Subsequently, we applied a sample to the filter and rinsed each sample tube four times into the manifold with the 5% TCA solution using a cornwall syringe set for 1 ml. We then washed the filters twice with 5% TCA by filling the manifold wells rapidly while the vacuum was on. We dried the filters by turning off the vacuum and filling each well of the manifold with 70% ethanol, allowing the filters to stand for about 15 seconds before reapplying the vacuum.

Subsequently, we placed the filters under a heat lamp for 10-20 minutes to dry. The dried filters were placed in 18 ml scintillation vials (Beckman Instruments, Wakefield, Mass.). We then added 10-12 ml of Betafluor scintillation fluid for counting (National Diagnostics, Manville, N.J.) to each vial and capped the vials. We also tested each sample using a non-specific poly (dA)-oligo(dT):z.s template.

We calculated assay results by subtracting dA counts/min from rA counts/min and then multiplying the result by 7.5 to convert to net counts/min/ml of original culture supernatant sample. Samples having values of $10^3$ counts/min/ml or greater were considered positive for HIV-1.

D24 ELISA

We tested N-butyl DNJ and AZT as inhibitors of viral replication in a p24 ELISA (enzyme linked immunosorbent assay). Detection of the HIV p24 antigen has been associated with progression to AIDS and has been proposed as one important end point in the evaluation of candidate antiretroviral drugs. Spector et al., *J. Infect. Dis.* 159, 822-28 (1989).

Specifically, we sampled cell-free culture supernatant fluid for p24 antigen as follows. We obtained an assay kit [HIV p24 Core Antigen ELISA, Catalogue Nos. NEK-045, NEK—046 and NEK—047, DuPont-NEN Research Products, Billerica, Massachusetts], according to the protocol included with the kit, which contains rabbit polyclonal antibodies to p24 antigen immobilized to microplate wells to capture any p24 antigen lysed from a test sample. The captured p24 antigen was complexed with biotinylated polyclonal antibodies to p24 antigen and probed with a streptavidin-horseradish peroxidase conjugate. We then incubated the complex with orthophenyldiamine-HCl, which produces yellow color proportional to the amount of p24 antigen captured. We then measured the absorbance of each well using a microplate reader and calibrated against the absorbance of a p24 antigen standard curve.

Mathematical Analysis Of Drug Interactions

We evaluated the agent interactions by the median effect principle and the isobologram technique with computer software using an IBM-PC (Armonk, N.Y.) [Chou et al. "Dose-Effect Analysis With Microcomputers: Quantitation of $ED_{50}$, $LD_{50}$, Synergism And Antagonism, Low-Dose Risk, Receptor Binding And Enzyme Kinetics". A Computer Software For Apple II Or IBM PC (Elsevier Biosoft, Cambridge, England, 1986)]. A multiple drug effect analysis [T. C. Chou and P. Talalay, *Adv. Enzyme Regul.*, 22, pp. 27–55 (1984)] was used to calculate combined agent effects. This method involves the plotting of dose-effect curves for each agent and for multiply-diluted fixed-ratio combinations of the agents using the median effect equation. Based on this method, we determined the combination index (CI) for various combinations according to this invention. CI values were determined from the median-effect plot parameters m(slope) and $D_m(ED_{50})$ of each agent and their combination based on the isobologram equation.

A combination index value of less than 1 indicates synergy, while a value equal to 1 indicates additive effects and a value greater than 1 indicates antagonism as previously defined herein. We also analyzed the data by the isobologram technique, which evaluates drug interactions by a dose-oriented geometric method.

The following representative data are expressed as either ng of protein/ml or ng of protein/viable cell number $\times 10^6$ (to exclude an anti-HIV-1 effect due to an anti-proliferative effect of the agent tested).

| | N-butyl DNJ/AZT in H9 Cells | | | | | |
| --- | --- | --- | --- | --- | --- | --- |
| | N-butyl DNJ (μM) | | | | | |
| AZT (μM) | 0 | .71 | 2.85 | 11.4 | 45.6 | 182.45 |
| | Day 7 Assay: p24 Antigen ELISA (ng/ml) | | | | | |
| 0 | 88.6 | 55.5 | 204.0 | 20.6 | 15.1 | 2.1 |
| .01 | 74.5 | 30.6 | | | | |
| .04 | 52.0 | | 14.9 | | | |
| .16 | 16.0 | | | 11.2 | | |
| .64 | 3.5 | | | | 0.6 | |
| 2.56 | 0.2 | | | | | 0.08 |
| | Day 7 Assay: p24 Antigen ELISA/Viable Cells (ng/cells $\times 10^6$) | | | | | |
| 0 | 31.3 | 21.9 | 82.3 | 7.0 | 6.2 | 0.7 |
| .01 | 25.4 | 8.9 | | | | |
| .04 | 15.3 | | 4.7 | | | |
| .16 | 5.7 | | | 3.4 | | |
| .64 | 1.1 | | | | 0.2 | |
| 2.56 | 0.05 | | | | | 0.03 |
| | Day 11 Assay: p24 Antigen ELISA (ng/ml) | | | | | |

N-butyl DNJ/AZT in H9 Cells

| AZT (μM) | N-butyl DNJ (μM) | | | | | |
|---|---|---|---|---|---|---|
| | 0 | .71 | 2.85 | 11.4 | 45.6 | 182.45 |
| 0 | 4125.0 | 4300.0 | 3850.0 | 3950.0 | 3650.0 | 365.0 |
| .01 | 4200.0 | 3850.0 | | | | |
| .04 | 4050.0 | | 3750.0 | | | |
| .16 | 3850.0 | | | 3600.0 | | |
| .64 | 3505.0 | | | | 154.5 | |
| 2.56 | 39.0 | | | | | 1.4 |

Day 11
Assay: p24 Antigen ELISA/Viable Cells (ng/cells × $10^6$)

| 0 | 5422.9 | 6231.9 | 7264.2 | 4817.1 | 4011.0 | 176.3 |
|---|---|---|---|---|---|---|
| .01 | 6461.5 | 5202.7 | | | | |
| .04 | 7500.0 | | 3571.4 | | | |
| .16 | 6416.7 | | | 3913.0 | | |
| .64 | 3074.6 | | | | 72.5 | |
| 2.56 | 18.8 | | | | | 0.8 |

Day 14
Assay: p24 Antigen ELISA (ng/ml)

| 0 | 2797.5 | 2940.0 | 2460.0 | 3000.0 | 2545.0 | 4170.0 |
|---|---|---|---|---|---|---|
| .01 | 3065.0 | 2635.0 | | | | |
| .04 | 2545.0 | | 2660.0 | | | |
| .16 | 2530.0 | | | 2785.0 | | |
| 64 | 3550.0 | | | | 4450.0 | |
| 2.56 | 2845.0 | | | | | 29.5 |

Day 14
Assay: p24 Antigen ELISA/Viable Cells (ng/cells × $10^6$)

| 0 | 5768.6 | 6000.0 | 5020.4 | 5660.4 | 4713.0 | 4088.2 |
|---|---|---|---|---|---|---|
| .01 | 6385.4 | 4705.4 | | | | |
| .04 | 6207.3 | | 3746.5 | | | |
| .16 | 5060.0 | | | 3129.2 | | |
| .64 | 4863.0 | | | | 4944.4 | |
| 2.56 | 2411.0 | | | | | 11.5 |

Day 11
Assay: Reverse Transcriptase Activity ($10^4$ CPM/ml)

| 0 | 510 | 680 | 680 | 660 | 610 | 130 |
|---|---|---|---|---|---|---|
| .01 | 500 | 690 | | | | |
| .04 | 510 | | 640 | | | |
| .16 | 660 | | | 600 | | |
| .64 | 560 | | | | 69 | |
| 2.56 | 19 | | | | | 0.47 |

Day 11
Assay: Reverse Transcriptase Activity/Viable Cells ($10^4$ CPM/cells × $10^6$)

| 0 | 685.2 | 985.5 | 1283.0 | 804.9 | 670.3 | 62.8 |
|---|---|---|---|---|---|---|
| .01 | 769.2 | 932.4 | | | | |
| .04 | 944.4 | | 609.5 | | | |
| .16 | 1100.0 | | | 652.2 | | |
| .64 | 491.2 | | | | 32.4 | |
| 2.56 | 9.1 | | | | | 0.3 |

*UNINFECTED CONTROL = 0

In acutely infected H9 cells, the combination of N-butyl DNJ ($\geq$45.6 μM) and AZT ($\geq$0.64 μM) inhibited HIV-1 synergistically without additive toxicity in vitro.

Mathematical evaluation of all the preceding data by the median-effect principle and the isobologram technique to determine the combination index (CI) values for AZT and N-butyl DNJ yielded the following values:

COMBINATION INDEX (CI) VALUES FOR AZT AND N-butyl DNJ

| Day | Assay | CI AT PERCENTAGE OF INHIBITION | |
|---|---|---|---|
| | | 90 | 95 |
| 7 | ELISA | .3998 | .4133 |
| 11 | ELISA | .2380 | .2270 |
| 7 | ELISA/$10^6$ Cells | .3889 | .4035 |
| 11 | ELISA/$10^6$ Cells | .2921 | .3265 |
| 11 | Reverse Transcriptase | .2799 | .2571 |
| 11 | Reverse Transcriptase/$10^6$ Cells | .4651 | .5154 |

The mathematical analysis of these results demonstrated that N-butyl-DNJ ($\geq$45.6 μM) and AZT ($\geq$0.64 μM) inhibited HIV-1 synergistically in acutely infected H9 cells in vitro. More specifically, the combination index values were less than 1 for 90-95% inhibition of viral replication on different harvest days, indicating synergism. No cellular toxicity of these agents, either alone or in combination, was noted in the uninfected drug-treated parallel control flasks.

The experiments reported above were repeated using the same cell types, assays, drugs and drug concentrations and the results were found to be reproducible.

While at present, the methods of demonstrating therapeutic effectiveness against HIV are controversial, it is currently recognized that anti-viral efficacy as shown by declines in p24 antigen levels and the decreased ability to isolate HIV from infected individuals may lead to increased survival and a decrease in the incidence of opportunistic infections. Therefore, based upon the aforementioned in vitro tests, it is expected that the combination drug and method of the present invention will be efficacious in the treatment of humans for AIDS or ARC attributable to HIV infection.

Pharmaceutical Compositions

While it is possible for the AZT and N-butyl DNJ active ingredients to be administered directly, it is preferable to present them as part of a pharmaceutical formulation. The formulations of the present invention comprise at least a synergistic combination of AZT and N-butyl DNJ in an amount which achieves antiviral efficacy together with one or more acceptable carriers thereof and optionally other therapeutic ingredients.

As used herein, "an amount which achieves antiviral efficacy" is an amount which is medically beneficial to the HIV infected patient but does not present toxic side effects which outweigh the benefits of its use.

While AZT is currently formulated for oral and intravenous administration, and N-butyl DNJ is currently formulated for oral administration, we know of no restrictions on their routes of administration or formulation.

Therefore, applicable formulations include those suitable for oral, rectal, nasal, topical (including buccal and sublingual), vaginal or parenteral (including subcutaneous, intermuscular, intravenous and intradermal) administration. The formulations may conveniently be presented in unit dosage form, e.g., tablets and sustained release capsules, and may be prepared by any methods well known in the art of pharmacy.

Such methods include the step of bringing into association the AZT and N-butyl DNJ with the carrier which constitutes one or more accessory ingredient. In general, the formulations are prepared by uniformly and intimately bringing into association the active ingredients with liquid carriers or finely divided solid carriers or both, and then if necessary shaping the product.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion and as a bolus, etc.

A tablet may be made by compression or molding, optionally with one or more accessory ingredients. Compressed tablets may be prepared by compressing in a suitable machine the active ingredients in a free-flowing form such as a powder or granules, optionally mixed with a binder, lubricant, inert diluent, preservative, surface-active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredients therein.

Formulations suitable for topical administration include lozenges comprising the ingredients in a flavored basis, usually sucrose and acacia or tragacanth; pastilles comprising the active ingredients in an inert basis such as gelatin and glycerin, or sucrose and acacia; and mouthwashes comprising the ingredients to be administered in a suitable liquid carrier.

Formulations suitable for topical administration to the skin may be presented as ointments, creams, gels, pastes, and transdermal patches comprising the ingredients to be administered and a pharmaceutically acceptable carrier.

Formulations for rectal administration may be presented as a suppository with a suitable base comprising, for example, cocoa butter or a salicylate.

Formulations suitable for nasal administration wherein the carrier is a solid include a coarse powder having a particle size, for example, in the range 20 to 500 microns which is administered in the manner in which snuff is taken, i.e., by rapid inhalation through the nasal passage from a container of the powder held close up to the nose. Suitable formulations wherein the carrier is a liquid, for administration, as for example, a nasal spray or as nasal drops, include aqueous or oily solutions of the active ingredients.

Formulations suitable for vaginal administration may be presented as pessaries, tampons, creams, gels, pastes, foams or spray formulations containing in addition to the active ingredients such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multidose containers, for example, sealed ampules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily sub-does, as herein above recited, or an appropriate fraction thereof, of the administered ingredients.

It should be understood that in addition to the ingredients particularly mentioned above the formulations of this invention may include other agents conventional in the art having regard to the type of formulation in question, for example, those suitable for oral administration may include flavoring agents.

Appropriate dosages for the AZT component of the combination of this invention in the treatment of AIDS or ARC can range from about 50 mg/day to about 1.2g/day. A more preferred range is about 200 mg/day to about 1000 mg/day. A still more preferred range is about 300 mg/day to about 800 mg/day.

Appropriate dosages for the N-butyl DNJ component of the combination of this invention in the treatment of AIDS or ARC may range from about 1 mg/kg/day to about 500 mg/kg/day. A preferred range is about 8 mg/kg/day to about 165 mg/kg/day. A more preferred range is about 20 mg/kg/day to about 130 mg/kg/day. A still more preferred range is about 25 mg/kg/day to about 100 mg/kg/day.

To obtain the benefits of the present invention, it is believed that suitable pharmaceutical formulations containing AZT and N-butyl DNJ should be prepared so that the ratio of these two ingredients ranges from about 1:50 to about 1:100 moles AZT:N-butyl DNJ. More preferred is a ratio of about 1:60 to about 1:80. Most preferred is a ratio of about 1:70 moles AZT to N-butyl DNJ.

The concentrations of N butyl DNJ and AZT required to fully inhibit HIV−1 replication, as single agents and in combination, vary in each experiment depending on the input virus inoculum, the cell type tested, and the sensitivity of the HIV−1 replicative assay used, as expected in biologic assays. However, synergistic effects between N-butyl DNJ ($>45.6$ μM) and AZT ($>0.64$ μM) were demonstrated easily.

While the data set forth in the examples are based on two specific forms of AZT and N-butyl DNJ, it is to be understood that any pharmaceutically acceptable salt of AZT or the free amine or pharmaceutically acceptable salt of N-butyl DNJ may be used in preparing or administering the combination of the present invention.

Further, while the pharmaceutical compositions of the present invention comprise both AZT and N-butyl DNJ in the same dosage form, it is to be understood that in practicing the method of the disclosed invention, the AZT and N-butyl DNJ may be administered in separate distinct dosage forms at different times, in separate distinct dosage forms, but essentially simultaneously, or together in the same pharmaceutical composition.

We claim:

1. A method of treating an HIV infected patient which comprises administering to said patient a combination of 3′-azido-3′-deoxythymidine and N-butyl deoxynojirimycin, or their pharmaceutically acceptable salts, in an amount which achieves antiviral efficacy and which yields a dose level which produces a combination index less than 1.

2. The method according to claim 1 wherein the 3′-azido-3′-deoxythymidine is administered to said patient in an amount from about 50 mg/day to about 1.2 g/day.

3. The method according to claim 1 wherein the 3′-azido-3′-deoxythymidine is administered to said patient in an amount from about 200 mg/day to about 1000 mg/day.

4. The method according to claim 1 wherein the 3'-azido-3'-deoxythymidine is administered to said patient in an amount from about 300 mg/day to about 800 mg/day.

5. The method according to claim 1 wherein the N-butyl deoxynojirimycin is administered to said patient in an amount from about 1 mg/kg/day to about 500 mg/kg/day.

6. The method according to claim 1 wherein the N-butyl deoxynojirimycin is administered to said patient in an amount from about 8 mg/kg/day to about 165 mg/kg/day.

7. The method according to claim 1 wherein the N-butyl deoxynojirimycin is administered to said patient in an amount from about 20 mg/kg/day to about 130 mg/kg/day.

8. The method according to claim 1 wherein the N-butyl deoxynojirimycin is administered to said patient in an amount from about 25 mg/kg/day to about 100 mg/kg/day.

9. The method according to claim 1 wherein the combination is administered to said patient orally.

10. The method according to claim 1 wherein the combination is administered to said patient intravenously.

11. The method according to claim 1 wherein the molar ratio of 3'-azido-3'-deoxythymid N-butyl deoxynojirimycin administered to said patient ranges from about 1:50 to about 1:100.

12. The method according to claim 1 wherein the molar ratio of 3'-azido—3'-deoxythymidine to N-butyl deoxynojirimycin administered to said patient ranges from about 1:60 to 1:80.

13. The method according to claim 1 wherein the molar ratio of 3'-azido-3'-deoxythymidine to N-butyl deoxynojirimycin administered to said patient is about 1:70.

14. The method according to claim 1 wherein the 3'-azido-3'-deoxythymidine and the N-butyl deoxynojirimycin are administered to said patient in separate, distinct dosages.

15. The method according to claim 1 wherein the 3'-azido-3'-deoxythymidine and the N-butyl deoxynojirimycin administered to said patient are combined in a single dosage form.

16. A pharmaceutical composition containing a combination of 3'-azido-3-deoxythymidine and N-butyl deoxynojirimycin, or their pharmaceutically acceptable salts, in an amount which achieves antiviral efficacy and which yields a dose level which produces a combination index less than 1.

17. The pharmaceutical composition according to claim 16 wherein the molar ratio of 3'-azido-3'-deoxythymidine to N-butyl deoxynojirimycin in said composition is from about 1:50 to about 1:100.

18. The pharmaceutical composition according to claim 17 wherein the molar ratio is from about 1:60 to about 1:80.

19. The pharmaceutical composition according to claim 17 wherein the molar ratio is about 1:70.

20. The pharmaceutical composition of claim 16 formulated for oral administration.

21. The pharmaceutical composition of claim 16 formulated for intravenous administration.

* * * * *